United States Patent [19]

Kuhrts

[11] Patent Number: 5,445,826

[45] Date of Patent: Aug. 29, 1995

[54] DELIVERY SYSTEM CONTAINING A GEL-FORMING DIETARY FIBER AND A DRUG

[75] Inventor: Eric H. Kuhrts, Santa Barbara, Calif.

[73] Assignee: CIBUS Pharmaceutical, Inc., Redwood City, Calif.

[21] Appl. No.: 167,325

[22] Filed: Dec. 14, 1993

Related U.S. Application Data

[63] Continuation of Ser. No. 850,942, Mar. 13, 1992, abandoned, which is a continuation-in-part of Ser. No. 440,656, Nov. 22, 1989, Pat. No. 5,118,510, and a continuation-in-part of Ser. No. 440,730, Nov. 22, 1989, Pat. No. 5,096,714, and a continuation-in-part of Ser. No. 440,728, Nov. 22, 1989, Pat. No. 5,023,245, which is a continuation-in-part of Ser. No. 212,715, Jun. 28, 1988, Pat. No. 4,965,252.

[51] Int. Cl.$^6$ ............................................. A61K 9/48
[52] U.S. Cl. ........................... 424/451; 424/464; 424/489; 424/490; 424/493; 424/494; 424/496
[58] Field of Search ............... 424/451, 484, 485, 496, 424/489, 439, 464, 466, 490

[56] References Cited

U.S. PATENT DOCUMENTS

| | | | |
|---|---|---|---|
| 1,891,698 | 12/1932 | Tuvin | 424/439 |
| 3,082,091 | 3/1963 | Smith | 424/466 |
| 4,756,911 | 7/1988 | Drost | 424/488 |
| 4,824,672 | 4/1989 | Day | 514/960 |
| 4,844,905 | 7/1989 | Ichikawa | 424/466 |
| 4,929,448 | 5/1990 | Ibsen | 424/489 |

OTHER PUBLICATIONS

Pharmacognosy, Tyler, V. E. ed., 7th edition, 1976.

Primary Examiner—D. Gabrielle Phelan
Attorney, Agent, or Firm—Cooley, Godward Castro, Huddleson & Tatum

[57] ABSTRACT

A prolonged-release unit dosage formulation or pharmaceutical composition, preferably in tablet form, is described. The composition consists essentially of a gel-forming fiber, preferably hydrocolloid-coated, a biologically-absorbable drug or other active therapeutic agent which is also preferably hydrocolloid-coated, a mineral salt which releases a physiologically-acceptable gas upon ingestion, preferably carbon dioxide, e.g., a mineral carbonate or bicarbonate, and optionally an organic or phosphoric acid and a dextrose or like soluble sugar. The fiber-containing composition, when in the form of a tablet or other unit dosage form together with the drug or agent and the stated disintegrants, provides a unique, efficient and controllable prolonged-action drug-delivery system.

10 Claims, No Drawings

DELIVERY SYSTEM CONTAINING A GEL-FORMING DIETARY FIBER AND A DRUG

CROSS-REFERENCE TO RELATED APPLICATIONS

This application is a continuation of U.S. application Ser. No. 07/850,942, filed 13 Mar. 1992, now abandoned, which is a continuation-in-part of U.S. application Ser. No. 07/440,656, filed 22 Nov. 1989, issued as U.S. Pat. No. 5,118,510, and a continuation-in-part of U.S. application Ser. No. 07/440,730, filed 22 Nov. 1989, issued as U.S. Pat. No. 5,096,714, and a continuation-in-part of U.S. application Ser. No. 07/440,728, filed 22 Nov. 1989, issued as U.S. Pat. No. 5,023,245, which is a continuation-in-part of U.S. application Ser. No. 07/212,715, filed 28 Jun. 1988, issued as U.S. Pat. No. 4,965,252.

BACKGROUND OF THE INVENTION

Field of the Invention and Prior Art

The present invention relates to novel prolonged release formulations or compositions, e.g., tablet, granule, lozenge, capsule, or like formulations, containing a gel-forming dietary fiber and a drug or other active therapeutic agent plus certain essential disintegrants.

Many drugs and vitamins must be released in a uniform and/or continuous manner over a period of time. Water-soluble vitamins, for example, unless placed into a time-release form, are almost immediately released into the bloodstream once they dissolve in the stomach. Aspirin is frequently coated to minimize gastric upset and release the drug over a period of time. Sustained-release dosage forms also avoid the necessity of frequent administration of the drug while, at the same time, achieving a desired blood level of active ingredient.

Various cellulose derivatives have been used to provide rapid disintegration of tablets, such as in U.S. Pat. No. 3,266,992, which describes the use of methylcellulose, sodium carboxymethylcellulose and hydroxyethylcellulose for such purpose. However, in contrast, hydroxypropylmethylcellulose in enteric coatings has been disclosed in U.S. Pat. No. 2,887,440 to prevent disintegration of a tablet core and delay release of the active ingredients.

U.S. Pat. No. 3,870,790 discloses a method of preparing a long-acting buccal composition for administering a therapeutic agent using an effective amount of hydroxypropylmethylcellulose which has been subjected to controlled humidity. Other processes for treating cellulose derivatives are described in U.S. Pat. Nos. 4,226,849, 4,357,469, 4,369,172, 4,389,393, 4,540,566, 4,795,327, and 4,849,229, the treated cellulose derivatives then being used in a solid drug dosage unit form to produce a controlled and prolonged-release pattern of a drug upon administration thereof.

For purposes of definition in this specification, the term "dietary fiber" is defined as "remnants of plant cells resistant to hydrolysis by the alimentary enzymes of man, the group of substances that remain in the ileum but are partly hydrolyzed by bacteria in the colon", according to JAMA 262, No. 4, 542–546 (Jul. 28, 1989) in the Council Report entitled "Dietary Fiber and Health", at page 542. This article, moreover, gives considerable information as to what constitutes a "dietary fiber" and is accordingly incorporated herein by reference.

Gel-forming dietary fibers include mucilages, plant gums, pectins or pectic substances, and lignin, all of which are endogenous compounds of plant materials which are resistant to digestion by enzymes in the monogastric stomach or small intestine. Chemically, nearly all of these plant materials are carbohydrates composed of repeating monosaccharide (sugar) units. Disaccharides have two sugar units, oligosaccharides three to twelve, and polysaccharides may contain a million or more. The water-soluble fractions of these substances form gels in the stomach and intestinal tract and are known to lower serum cholesterol.

Gums and mucilages have no common structure but are polysaccharides containing several sugars with alternating monomer structures and may or may not contain uronic acids. There are many gums found in plants and cereal grains. Guar and locust bean gums are galactomannans, whereas gum arabic is an acidic polymer of galactose and rhamnose. Oat and barley contain gums, but are not practical for use in the present application because of the low percentage of active gum per weight volume. Most of the gums in the present application are effective at much lower dosages. Suitable gums include, inter alia, besides guar gum, the following: locust bean gum, acacia gum, gum arabic, xanthan gum, carrageenan gum, karaya gum, tragacanth gum, and ghatti gum.

Pectic substances or pectins are mixtures of polysaccharides of partially methylated and 1,4-D galacturonic acid units with side chains containing arabinose, galactose, xylose, and rhamnose. They are contained in many fruits and vegetables as well as in other plants.

Other suitable gel-forming dietary fibers include psyllium husks, algal polysaccharides, glucomannan, and agar, to name a few. Lignin is a non-carbohydrate polymer of aromatic plant alcohols comprising oxygenated phenylpropane units. As a plant matures, more lignin is produced, which acts as a sort of cement as it hardens and holds together other plant cell wall constituents. Lignin passes through the digestive tract with very little change.

As already mentioned, a recent review of dietary fiber which mentions these substances is contained in the following reference: Dietary Fiber and Health, JAMA 262: No. 4, 542–546 (1989), from the Council on Scientific Affairs, American Medical Association.

Some gel-forming fibers such as guar gum are used as binders and disintegrators for compressed tablets, but at fairly low levels. At higher levels, these gel-forming fibers and gums are known not to dissolve properly when compressed into tablets.

Various unsuccessful attempts have been made to solve the problem of improper and incomplete dissolution of guar gum tablets. EPA 0080673 describes these problems in detail, and discloses the use of 5 to 30% of highly-dispersed silica gel in guar tablets. Normally used tablet disintegrants or additives such as polyvinylpyrrolidone (crosslinking agent), sodium carboxymethyl-starch, cornstarch, microcrystalline cellulose, and so on, do not lead to satisfactory results. Hard tablets are produced which do not swell properly, and which form an impenetrable layer of gel around a powder core which may pass through the gastrointestinal tract undissolved and nearly intact.

U.S. Pat. No. 4,824,672 describes the use of mineral carbonates to enhance dispersion of gel-forming dietary fibers in orally-administrable pharmaceutical compositions for use in reducing serum cholesterol levels. Such compositions have proved to be effective in use for their intended purpose of dispersing the fibers, but do not disclose or suggest a method or means for providing a controllable prolonged-release unit dosage formulation of a biologically-absorbable therapeutic agent or drug.

The foregoing EPO 0080673 mentions the employment of citric acid with guar gum tablets. The citric acid and sweeteners were used, according to that disclosure, to improve the acceptability of the tablets if they were to be chewed. Accordingly, the citric acid was there used to provide flavor and an aromatic quality to the product. Such formulations did not contain a mineral carbonate or bicarbonate and, moreover, when a carboxylic acid such as citric acid was employed in the compositions of that invention, "the acid is coated with 1 to 20% of a water-repellent agent based on the weight of the acid", reportedly to provide increased storage stability of the product.

It is apparent that the prior art has not provided any suitable prolonged-release unit dosage formulation for the prolonged release of an effective dose of a biologically-absorbable therapeutic agent or drug, much less such a prolonged-release unit dosage formulation which employs or embodies a gel-forming dietary fiber as an essential part of the matrix, fundamentally because of the fact that the swelling and balling and plug formation of such gel-forming dietary fibers has heretofore been considered an insurmountable disadvantage, insofar as the acid of the stomach does not readily or uniformly dissolve dietary fiber formulations, especially when in unit dosage form such as a tablet, granule, capsule, lozenge, or the like, for which reason release of any therapeutic agent or drug which may have been combined therewith was unpredictable and non-uniform and generally insufficiently rapid to cause or permit release of all of the drug or other therapeutic agent content thereof while the unit dosage formulation was present in the gastrointestinal tract.

According to my previous invention of U.S. Ser. No. 07/440,730, now U.S. Pat. No. 5,096,714, the entire disclosure of which copending application is hereby referred to and, by reference, made a part hereof, however, excellent prolonged-release unit dosage formulations were provided, which consisted essentially of an effective dose of the selected biologically-absorbable therapeutic agent or drug, a gel-forming dietary fiber, and a physiologically-acceptable edible acid, preferably a food-grade organic acid or phosphoric acid, and a mineral salt which releases a physiologically-acceptable gas upon ingestion, preferably a mineral carbonate or bicarbonate which releases carbon dioxide upon ingestion. According to my previous patent, as stated therein "when a biological liquid begins to penetrate or wick into the prolonged-release unit dosage formulation, it dissolves the acid and mineral salt present therein, which react together to cause a rapid evolution of gas, e.g., carbon dioxide, which cannot be effected using either stomach acid alone or the mineral salt alone. This rapid evolution of gas breaks up the prolonged-release unit dosage form, e.g., tablet, granule, capsule, lozenge, or the like, before a surface layer of gel can form around the unit dosage form, especially a tablet, from the normal reaction of the gel-forming dietary fiber, which surface layer of gel would seal the unit dosage form off from further hydration and disintegration. As already stated, stomach acid alone is not sufficiently rapid acting and is furthermore outside of the unit dosage form, so that it is necessary to have both the physiologically-acceptable edible acid and the mineral salt which releases a physiologically-acceptable gas upon ingestion, inside the tablet, granule, capsule, lozenge, or the like, or dispersed throughout the tablet, granule, capsule, lozenge, or other unit dosage form, to increase the speed of hydration of the drug or other therapeutic agent contained in the unit dosage formulation. According to the invention, the gel produced by the gel-forming dietary fiber modulates the release of the drug, but does not prevent the drug from being biologically absorbed, inhibition of disintegration by formation of a gel coating around the unit dosage formulation by the gel-forming dietary fiber being prevented by the evolution of a physiologically-acceptable gas by virtue of the combined action of the acid and mineral salt within the unit dosage formulation itself upon contact with biological fluids, e.g., those of the gastrointestinal tract."

According to the present invention, the presence of a mineral carbonate or bicarbonate in the formulation provides an improved hydration rate and helps to open up the selected solid unit dosage form involved, allowing for more rapid hydration which assists with controlled release of the biologically-absorbable therapeutic agent or drug contained therein, but may be used in lower percentages when more prolonged release is desired. Likewise, the physiologically-acceptable acid, e.g., the food-grade organic acid or phosphoric acid, has been found not to be absolutely essential, although it can be present to assist in providing an improved hydration rate and help to open up the tablet or other selected oral unit-dosage form involved when a quicker release of drug is desired. It is unnecessary when a more prolonged release is desired.

The employment of these ingredients, in the manner described, plus the precoating of one or both of the gel-forming fiber particles employed and the drug or other therapeutic agent particles involved, permits the percentage of fiber in the formulation to be lower, whereas the ratio of other excipients to fiber may be higher, and this precoating of the fiber and drug, as well as the additional variable and optional possible variations in the other ingredients present, provides an improved manner of dealing with the problem of getting the tablet or other oral unit dosage form to hydrate properly, albeit in a different manner according to the present invention, according to which the guar gum or other gel-forming fiber is actually employed to produce controlled release of the therapeutic agent or drug by controlling the rate of hydration of the fiber so that the gel fiber matrix remains relatively intact and may even pass entirely through the gastrointestinal tract, slowly releasing the therapeutic agent or drug as it passes through the system. Accordingly, according to the present invention, I have been able to utilize the long-outstanding problem of improper and incomplete dissolution of guar gum or other gel-forming fiber tablets or other pharmaceutical forms, as pointed out previously under the heading "Field of Invention and Prior Art", to advantage. Instead of hard tablets, granules, etc., which do not swell properly and in which the gel-forming fiber forms an impenetrable layer around a powder or other core which passes through the gastrointestinal tract undissolved, I have been able to produce controlled release of the therapeutic agent or drug from the gel-forming fiber matrix so that, as the gel-forming fiber matrix passes through the gastrointestinal tract, the therapeutic agent or drug is subjected to controlled release as desired, the expendable fiber matrix, especially when precoated, passing through the gastrointestinal tract and being eliminated in the feces after performing its predesignated function of producing predetermined controlled release of the therapeutic agent or drug as it passes through the gastrointestinal tract.

Many important and variable classes of therapeutic agents and drugs, including also peptides and liposoluble drugs, can be transported and subjected to controlled release according to the present invention, in which the percentage of the gel-forming fiber present, especially when precoated, and due to a different function than in previous developments, can be substantially lower than previously believed possible. The novel prolonged-release unit dosage form of the present invention releases the drug or other therapeutic agent in a manner which can be precontrolled and which does not require complete disintegration of the tablet or other oral unit dosage form involved, as previously believed, because the tablet or other unit dosage form need not break up in the gastrointestinal tract but rather can remain essentially solid until it is expelled therefrom, meanwhile controllably releasing the drug or other therapeutic agent on route to its point of elimination. Aside from the usual advantages of controllable prolonged release rate, the present invention also provides a way to protect peptides, proteins, liposoluble drugs, vitamins, and the like, from premature disintegration or deterioration while in the gastrointestinal tract, and for reducing irritation therein by non-steroidal as well as other anti-inflammatory and similar agents which are capable of producing gastric irritation and ulceration due to chronic therapy therewith over a period of time, as will be apparent to one skilled in the art.

The following additional comments are appropriate:

It is known that the particle size distribution of gel-forming fibers such as guar gum has a direct effect on viscosity. It has also been found that the finer the particle size of the guar gum or other gel-forming fiber, the more difficult or impossible it becomes to get tablets containing a high percentage of gel-forming fiber or gum to disintegrate, hydrate, or dissolve.

Gel-forming fibers such as guar gum have been used as tablet disintegrants, but at low levels, generally less than 5%, optimally around 3%. A disintegrant helps a tablet to break down and release the drug rapidly, usually within 20 minutes. As grades of gums or fibers increase in viscosity, the drug-release rate will generally decrease. The lower viscosity grades have a faster solution rate than higher viscosity grades. Therefore, it is necessary to be able to have a consistent granulation of gel-forming fiber or gum for a consistent release pattern of drug. This, in turn, leads to greater control over the viscosity of the tablet as it travels in the gastrointestinal tract. Generally speaking, disintegrating agents with the highest rates of water absorption produce the longest disintegration time, although this is also related to the percentage of disintegrant used in the formulation. Gel-forming fibers such as guar gum produce rapid dissolution (e.g., 20 minutes) when used at a 3% level in a formulation, but above a 5% level start locking up the tablet and slowing down dissolution, even preventing the tablet from completely dissolving or hydrating. I have turned this disadvantage into an advantage according to the present invention.

According to the present invention, which I consider to be an advancement in the art and a further extension of the invention of my previous U.S. Pat. No. 5,096,714, I combine in a unit dosage form, e.g., tablet, the gel-forming fiber and the drug or other therapeutic agent, and an amount of a mineral salt which releases a physiologically-acceptable gas upon ingestion, e.g., a mineral carbonate or bicarbonate, and may include other normal pharmaceutical excipients. For certain results, I also include a pharmaceutically-acceptable organic acid or phosphoric acid. Additionally, for certain purposes, I may also include a pharmaceutically-acceptable soluble sugar. In addition, I may coat the gel-forming fiber and optionally the drug or other therapeutic agent with a film of hydrocolloid, which may be the same or different than the gel-forming fiber employed. In this manner, I am able to control the release rate of the drug or other therapeutic agent from the fiber matrix over a wide range, which has not heretofore been possible using the same or similar ingredients. For example, for a relatively quick-release tablet, or a tablet in which the bulk of the therapeutic agent is released relatively quickly while the remainder is released over an approximately eight (8) hour period, I may coat the gel-forming fiber particles with a film of the hydrocolloid and I may employ a smaller amount of mineral carbonate or bicarbonate. I may also employ an organic acid, such as citric acid, or phosphoric acid, to facilitate a more rapid release. In addition, a soluble sugar may be included. When I wish an even more rapid release, I may provide the hydrocolloid film coating on both of the gel-forming fiber particles and the drug or other therapeutic agent particles. I may also increase the amount of the mineral carbonate or bicarbonate and the amount of the organic or phosphoric acid present in the composition. When I wish to provide a shorter release time for the drug or other therapeutic agent, I may employ a hydrocolloid film coating on only the gel-forming fiber particles, or eliminate the hydrocolloid film entirely, and/or reduce the amount of mineral carbonate or bicarbonate employed and/or eliminate the organic acid or phosphoric acid completely. In this manner, I am able to provide either extremely long-acting or relatively short-acting pharmaceutical forms, and to control the release times and rates by controlling the amounts of the ingredients employed, as just representatively pointed out in the foregoing.

The degree and rapidity of release of the drug or other therapeutic agent may also be controlled by controlling the relative amounts and types of gel-forming fiber employed, as it is well known that some are more soluble and swellable than others. The soluble and swellable types are of by far the greatest interest according to the invention. All in all, by exploiting the various possible variables as set forth in the foregoing, and as will be readily apparent to one skilled in the art, I am able to provide a unit dosage form from which the drug or other therapeutic agent is released in a controlled manner over an extremely wide range of time periods, with of course the ensuing result that the drug or other therapeutic agent is released to a different extent in different segments of the gastrointestinal tract.

OBJECTS OF THE INVENTION

It is an object of the invention to provide a novel and advantageous prolonged-release unit dosage formulation and a method for prolonging the release of a drug or other active therapeutic agent upon administration to a human being involving the employment of such improved and advantageous prolonged-release unit dosage formulation of the invention. Another object of the invention is to provide such formulation and method which involve the employment of a prolonged-release unit dosage formulation consisting essentially of an effective dose of a biologically-absorbable drug or other therapeutic agent and a gel-forming dietary fiber, either the fiber or both of which may be particularly precoated, and a mineral salt which releases a physiologically-acceptable gas upon ingestion, and which optionally includes a physiologically-acceptable edible acid. A further object of the invention is the provision of such formulation and method wherein the disadvantageous characteristics of the gel-forming dietary fiber matrix can be offset by the inclusion therein of a mineral salt which releases a physiologically-acceptable gas upon ingestion, preferably a mineral carbonate or bicarbonate which releases carbon dioxide upon ingestion, and only optionally a physiologically-acceptable edible acid, preferably a food-grade organic acid or phosphoric acid, a major concept according to the present invention being the optional and preferable precoating of the gel-forming fiber particles either alone or as well as the drug or other active therapeutic agent employed. Still an additional object is the provision of such a formulation and method wherein the unit dosage formulation optionally also contains a soluble sugar to enhance the controllable disintegration of the unit dosage formulation upon ingestion in addition to providing a more generally acceptable flavor. A still further object is to provide a novel and advantageous prolonged-release unit dosage formulation and a method for prolonging the release of a drug or other active therapeutic agent upon administration to a human being involving the employment of such improved and advantageous prolonged-release unit dosage formulation of the invention, consisting essentially of an advantageously precoated gel-forming fiber matrix and a biologically-absorbable therapeutic agent or drug, which therapeutic agent or drug may also advantageously be precoated, said prolonged-release unit dosage form and method of using the same being highly advantageous from the standpoint of not requiring complete disintegration of the unit dosage form for it to be effective (as previously believed necessary) and, moreover, permitting controlled release of the drug or other active therapeutic agent in selected portions of the gastrointestinal tract whereas the matrix, or a substantial portion thereof, can pass substantially intact through the gastrointestinal tract and be ultimately expelled there-from. Other objects include the provision of novel protective and prolonged-release dosage formulations and methods of using the same for the protection of pharmacologically-active contents thereof against premature destruction in the gastrointestinal tract and for the protection of the gastrointestinal tract against irritation by pharmacologically-active ingredients which are prone to cause the same. Still other objects will be apparent to one skilled in the art and additional objects will become obvious as this specification proceeds.

THE INVENTION

The present invention relates, inter alia, to the unexpected discovery that by precoating the gel-forming fiber or gum particles, and optionally but advantageously also the drug or other therapeutic agent particles, with a film of Sodium Carboxymethylcellulose (NACMC) or other hydrocolloid, including hydrocolloids such as, e.g., natural and modified gums, celluloses and modified celluloses, pectin, mucillages, modified starches, noncellulosic polysaccharides, algal polysaccharides, and mixtures thereof, particularly preferred hydrocolloids including carboxymethyl cellulose, methyl cellulose, karaya gum, acacia gum, sodium alginate, calcium alginate, hydroxypropylmethylcellulose, and mixtures thereof, and then tableting or granulating together with a mineral carbonate or bicarbonate to speed up hydration, the locking up or sealing from further hydration can be prevented and a smooth and controlled release of the active drug or agent can be achieved.

Furthermore, it is an additional attribute of this development to provide for a quicker controlled-release of drug (i.e., 2 to 3 hours) than can be achieved when the gel-forming fiber is not precoated. In addition, precoating the gel-forming fiber allows both lower and higher percentages of the fiber to be used in the formula.

The release characteristics of the drug when a gel-forming fiber such as guar gum is used as an excipient can be depicted with a bell shaped curve. Good disintegration time is achieved from 1% to about 10%, but then starts going down above 10% until there is reduced disintegration and further hydration of the tablet because it begins to lock up. Tablets exhibiting this phenomenon have a film of gel on the surface with a powder core. The film of hydrated gel tends to seal the rest of the tablet from further hydration, or at least slows down the hydration considerably. This is true whether the drug is a water soluble drug, a slightly water-soluble drug, or a water insoluble drug. Coating of the fiber particles with a film of hydrocolloid keeps this from occurring when you do not wish it to do so. The optional coating of the drug or other therapeutic agent with a film of hydrocolloid also assists in a smooth and even release of the drug or agent over a somewhat less extended period.

The apparent negative effect of gelation can thus be used to produce controlled-release of a drug, especially if, as in the following examples, one can obtain greater control of the hydration of the tablet, granule, etc., through coating the gel-forming fiber or gum particles. Mineral carbonate or bicarbonate, when present, increases the rate of drug release. The thus-designed tablet does not need to disintegrate to release the active therapeutic agent or drug, but can retain its shape and integrity as a tablet while gelling and swelling slightly. The drug is then slowly released from this gel matrix. Such a delivery system has a wide degree of control depending on whether one desires to deliver the majority of the drug in a few hours or over a longer period, e.g., 8 to 12 hours.

The Physiologically-Acceptable Acid—Optional and Preferable Only

As physiologically-acceptable acid may be employed any non-toxic and preferably edible acid such as citric, malic, succinic, ascorbic, fumaric, phosphoric, tartaric, gluconic, acetic, tannic, lactic, glycollic, or the like. Food-grade organic acids are preferred and, of organic food-grade acids, citric, tartaric, and malic are preferred due to their introduction of a definite citrus, grape, and apple flavor into the composition, respectively.

The Gel-Forming Dietary Fiber—Essential

According to the invention, any of the foregoing enumerated gel-forming dietary fibers may be employed, with gums such as guar gum and the like and psyllium seed husks in powdered form being preferred, but pectin or a pectic substance, algal polysaccharides, glucomannan, agar, lignin, or the like, or combinations thereof, may generally be employed with essentially the same results.

The Mineral Salt—Essential

According to the invention, any physiologically-acceptable mineral salt which releases a physiologically-acceptable gas upon ingestion may be employed. Such gas released is preferably carbon dioxide and the mineral salt is preferably a mineral carbonate or bicarbonate, with calcium carbonate, magnesium carbonate, magnesium bicarbonate, sodium carbonate, and sodium bicarbonate, as well as the corresponding potassium carbonate and bicarbonate, being preferred.

Soluble Sugar—Optional Only

As the optional but most preferred soluble sugar employed to assist disintegration according to the invention any of the following representative sugars may be employed: Dextrose, sucrose, glucose, xylose, ribose, mannose, galactose, fructose, maltose, partially hydrolyzed starch, corn syrup solids, sugar alcohols such as sorbitol, xylitol, mannitol, and the like, with dextrose, xylose, and fructose being preferred.

The Hydrocolloid

Hydrocolloids are organic polymers containing numerous hydrophilic groups such as —OH, —COOH, —$SO_4$, —$PO_4$, and —$NH_2$. They may be vegetable gums such as tragacanth or animal protein such as gelatin. They are capable of uniting with water, and dissolve or swell in the presence of water.

Hydrocolloids useful in the present invention are water-soluble or water-swellable polymeric substances such as cellulosic polymers and gums. It is to be understood that any hydrocolloid may be employed according to the present invention. By way of example, suitable cellulosic polymers are cellulose ethers such as methyl cellulose, cellulose alkyl hydroxylates such as hydroxymethyl cellulose and hydroxyethyl cellulose, cellulose alkyl carboxylates such as carboxymethyl cellulose and carboxyethyl cellulose, and alkali metal salts of cellulose alkyl carboxylates such as sodium carboxymethyl cellulose and sodium carboxyethyl cellulose. Examples of suitable gums are gum acacia, guar gum, xanthan gum, gum tragacanth, seaweed hydrocolloids, such as carrageenans (sodium carrageenate and mixtures of sodium, potassium and calcium carrageenates), and water-soluble alginates (sodium or ammonium alginates).

Tableting Pressures and Procedure

According to the invention, in producing tablets, usual tableting procedure and practice is employed, with pressures ranging from about 4,000 to about 10,000 pounds per square inch being preferred. Due to the fact that the gel-forming dietary fibers become closely compacted and even more difficult to disintegrate at higher tableting pressures, when tableting pressures above about 10,000 pounds per inch are employed, care must be taken that the possibility of hydration of the tablet is not impaired. To this end, cellulose flocked granules, microcrystalline cellulose, plain or chemically-modified starch, lactose, dextrose, mannitol, carboxymethylcellulose, methylcellulose, lubricants such as magnesium stearate or polyethylene glycols, or mineral excipients such as dicalcium phosphate, silicon dioxide, talc, and the like may be included singly or in combination in any desired ratio as a blend, but in any event only to the extent necessary and for the purpose of providing a tablet hardness sufficient for maximum tablet stability but not so great that the disintegration rate of the tablet in water or gastric fluid is disadvantageously affected.

Ranges of Ingredients

According to the invention, the range for the gel-forming dietary fiber comprising an essential part of the prolonged-release matrix of the present invention should be about 10% to 85% by weight, preferably about 35–50% by weight; the range for the mineral salt should be about 5% to about 75% by weight, preferably about 5–15% by weight; and the range of physiologically-acceptable edible acid should be about 0% to about 50% by weight, preferably about 2–5% by weight. The gel-forming fiber to drug weight ratio should be between about 1,000:0.5 and 1:1.5. Therapeutic agents which are employed in microgram dosages fall at the higher end of the range and therapeutic agents which require relatively larger amounts for a therapeutically-effective dose fall at the lower end of the range, as will be readily understood and as illustrated by the Examples herein. When present, the soluble sugar is preferably present in an amount between about 1 and about 30% by weight, preferably between about 3 and about 12% by weight.

SUMMARY OF THE INVENTION

The invention, then, comprises the following, inter alia, singly or in combination:

A solid prolonged-release oral unit dosage composition for oral administration and ingestion in solid form, and intended to be swallowed as such, which consists essentially of a solid admixture of an effective dose of a biologically-absorbable therapeutic agent or drug, a gel-forming dietary fiber matrix, a mineral salt which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being coated with a hydrocolloid film and the therapeutic agent or drug particles being optionally coated with a film of the same or a different hydrocolloid; such a composition wherein the gas released is carbon dioxide; such a composition wherein the mineral salt is a mineral carbonate or bicarbonate; such a composition wherein the mineral salt is calcium carbonate, magnesium carbonate, magnesium bicarbonate, sodium carbonate, sodium bicarbonate, potassium carbonate, or potassium bicarbonate; such a composition wherein the acid is present in amount of about 1% to about 50% by weight; such a composition wherein the acid is a food-grade organic acid or phosphoric acid; such a composition wherein the gel-forming dietary fiber comprises about 30–40% by weight of the composition; such a composition wherein a soluble sugar is present in an amount of about 1% to about 12% by weight of the composition; such a composition wherein the gel-forming fiber is psyllium husk powder, guar gum, locust bean gum, acacia gum, gum arabic, xanthan gum, carrageenan gum, karaya gum, tragacanth gum, ghatti gum, pectin, a pectic substance, an algal polysaccharide, glucomannan, agar, or lignin, or a combination of more than one thereof; such a composition wherein the drug or therapeutic agent is in granular form, with a hydrocolloid film coating about the granules thereof; such a composition wherein the hydrocolloid is a cellulose polymer, gum acacia, guar gum, xanthan gum, gum tragacanth, a carrageenan, or an alginate, or a combination of more than one thereof; such a composition wherein the drug or therapeutic agent is in granular form, with a hydrocolloid coating about the granules thereof, and wherein both the gel-forming fiber and the drug or therapeutic agent are coated with a film of a hydrocolloid which is cellulose polymer, gum acacia, guar gum, xanthan gum, gum tragacanth, a carrageenan, or an alginate, or a combination of more than one thereof; such a composition wherein at least the gel-forming dietary fiber is in the form of granules which are coated with a cellulose polymer coating, the composition optionally being compressed into a tablet form; such a composition wherein the drug or therapeutic agent is in granular form, the granules being coated with a film of a cellulose polymer, the composition optionally being compressed into a tablet form; such a composition wherein the drug or therapeutic agent is niacin; such a composition wherein the niacin is present in amount between about 100 and about 200 mg/per unit dosage form; such a composition in tablet form; and such a composition wherein the drug or therapeutic agent is an analgesic, an antihypercholesterolemic, a vitamin, a stimulant, an appetite suppressant, a mineral supplement, or a therapeutic peptide.

Moreover, a method for prolonging the release of a drug or therapeutic agent upon oral ingestion by a human being, comprising the step of orally administering to the said human being a prolonged-release unit dosage oral composition in solid form which consists essentially of a solid admixture of an effective dose of a biologically-absorbable therapeutic agent or drug, a gel-forming dietary fiber matrix, a mineral salt which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being coated with a hydrocolloid film and the therapeutic agent or drug particles being optionally coated with a film of the same or a different hydrocolloid; such a method wherein the gas released is carbon dioxide; such a method wherein the mineral salt is a mineral carbonate or bicarbonate; such a method wherein the mineral salt is calcium carbonate, magnesium carbonate, magnesium bicarbonate, sodium carbonate, sodium bicarbonate, potassium carbonate, or potassium bicarbonate; such a method wherein the acid is present in amount of about 1% to about 50% by weight; such a method wherein the acid is a food-grade organic acid or phosphoric acid; such a method wherein the gel-forming dietary fiber comprises about 30–40% by weight of the composition; such a method wherein a soluble sugar is present in an amount of about 1% to about 12% by weight of the composition; such a method wherein the gel-forming fiber is psyllium husk powder, guar gum, locust bean gum, acacia gum, gum arabic, xanthan gum, carrageenan gum, karaya gum, tragacanth gum, ghatti gum, pectin, a pectic substance, an algal polysaccharide, glucomannan, agar, or lignin, or a combination of more than one thereof; such a method wherein the drug or therapeutic agent is in granular form, with a hydrocolloid film coating about the granules thereof; such a method wherein the hydrocolloid is a cellulose polymer, gum acacia, guar gum, xanthan gum, gum tragacanth, a carrageenan, or an alginate, or a combination of more than one thereof; such a method wherein the drug or therapeutic agent is in granular form, with a hydrocolloid coating about the granules thereof, and wherein both the gel-forming fiber and the drug or therapeutic agent are coated with a film of a hydrocolloid which is cellulose polymer, gum acacia, guar gum, xanthan gum, gum tragacanth, a carrageenan, or an alginate, or a combination of more than one thereof; such a method wherein the gel-forming dietary fiber is in the form of granules which are coated with a cellulose polymer coating, the composition optionally being compressed into a tablet form; such a method wherein the drug or therapeutic agent is in granular form, the granules being coated with a film of a cellulose polymer, the composition optionally being compressed into a table form; such a method wherein the drug or therapeutic agent is niacin; such a method wherein the niacin is present in amount between about 100 and about 200 mg/per unit dosage form; such a method wherein the composition is in tablet form; and such a method wherein the drug or therapeutic agent is an analgesic, an antihypercholesterolemic, a vitamin, a stimulant, an appetite suppressant, a mineral supplement, or a therapeutic peptide.

Also, a solid prolonged-release oral unit dosage composition for oral administration and ingestion in solid form and intended to be swallowed as such, which consists essentially of an effective dose of an oil-soluble drug, vitamin, or other therapeutic agent, and a gel-forming dietary fiber, in which the oil-soluble drug, vitamin, or agent is entrapped or embedded in particles of the fiber, optionally in the form of a tablet; as well as a solid prolonged-release oral unit dosage composition for oral administration and ingestion in solid form and intended to be swallowed as such, which consists essentially of an effective dose of a biologically-absorbable therapeutic agent or drug in microsphere or nanosphere particle form, which is capable of being transported from the intestinal lumen or epithelium into the bloodstream in a matrix comprising a gel-forming dietary fiber, optionally in the form of a tablet; and such a composition wherein the nanosphere or microsphere contains a therapeutic peptide or protein and wherein the gel-forming dietary fiber is present in a pancreatic-enzyme activity-inhibitory amount so as to protect the peptide or protein from destruction by proteolytic degradation in the gastrointestinal tract upon oral administration.

Further, a solid prolonged-release oral unit dosage composition for oral administration and ingestion in solid form and intended to be swallowed as such, which consists essentially of an effective dose of a biologically-absorbable peptide or protein in a matrix comprising a gel-forming dietary fiber in a pancreatic-enzyme activity-inhibitory amount so as to protect the peptide or protein from destruction by proteolytic degradation in the gastrointestinal tract upon oral administration, optionally in the form of a tablet; such a composition wherein at least the peptide or protein is coated with a protective hydrocolloid coating; such a composition wherein the peptide or protein is present in the form of microsphere or nanosphere particles which are capable of being transported from the intestinal lumen or epithelium into the bloodstream upon ingestion; and such a composition wherein gel-forming dietary fiber particles are coated with a hydrocolloid and optionally compressed into the form of a tablet.

In addition, a method of reducing destruction by proteolytic degradation in the gastrointestinal tract upon oral administration of a therapeutic peptide or protein, which consists essentially of administering the same in the form of a solid prolonged-release oral unit dosage composition consisting essentially of an effective dose of the said therapeutic peptide or protein in a matrix comprising a gel-forming dietary fiber which is present in a pancreatic-enzyme activity-inhibitory amount so as to protect the peptide or protein from destruction by proteolytic degradation in the gastrointestinal tract, said composition optionally being in the form of a tablet; as well as a method of reducing irritation of the gastrointestinal tract caused by oral administration of a nonsteroidal anti-inflammatory drug, which consists essentially of the step of administering the drug in an oral dosage form comprising a gel-forming fiber matrix for protection of the epithelium and gastrointestinal lining upon ingestion, the gel-forming fiber being present in an epithelium- and gastrointestinal lining-protective amount; and such a method wherein gel-forming dietary fiber particles are coated with a hydrocolloid film and optionally compressed into the form of a tablet; as well as such a method wherein gel-forming dietary fiber particles are coated with a cellulose polymer film and optionally compressed into the form of a tablet.

Finally, a solid prolonged-release oral unit dosage composition for oral administration and ingestion in solid form, and intended to be swallowed as such, which consists essentially of a solid admixture of an effective dose of a biologically-absorbable therapeutic agent or drug, a gel-forming dietary fiber matrix, a mineral salt which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being optionally coated with a hydrocolloid film and the therapeutic agent or drug particles being optionally coated with a film of the same or a different hydrocolloid; such a composition wherein the gas released is carbon dioxide; such a composition wherein the mineral salt is a mineral carbonate or bicarbonate; such a composition wherein the mineral salt is calcium carbonate, magnesium carbonate, magnesium bicarbonate, sodium carbonate, sodium bicarbonate, potassium carbonate, or potassium bicarbonate; such a composition wherein the acid is present in amount of about 1% to about 50% by weight; such a composition wherein the acid is a food-grade organic acid or phosphoric acid; such a composition wherein the gel-forming dietary fiber comprises about 30–40% by weight of the composition; such a composition wherein a soluble sugar is present in an amount of about 1% to about 12% by weight of the composition; such a composition wherein the gel-forming fiber is psyllium husk powder, guar gum, locust bean gum, acacia gum, gum arabic, xanthan gum, carrageenan gum, karaya gum, tragacanth gum, ghatti gum, pectin, a pectic substance, an algal polysaccharide, glucomannan, agar, or lignin, or a combination of more than one thereof; such a composition wherein at least the gel-forming dietary fiber is in the form of granules which are coated with a hydrocolloid film coating, the composition optionally being compressed into a tablet form; and such a composition wherein the drug or therapeutic agent is in granular form, the granules being coated with a hydrocolloid film, the composition optionally being compressed into a tablet form.

DETAILED DESCRIPTION OF PREFERRED EMBODIMENTS

The following Examples are given to illustrate the compositions and method of the present invention, but are not to be construed as limiting.

EXAMPLE 1

Quick Controlled Release Tablet

Tablets containing the gel-forming fiber guar gum and Niacin, along with a mineral carbonate, an organic food-grade acid such as citric acid, and certain excipients, can act as a very effective "quick" controlled-release formulation. This composition virtually eliminates the unpleasant side effects such as flushing and itching due to Niacin. The tablet forms a soft gel which releases the Niacin as the fiber hydrates. A time-release assay of the Niacin indicates that the bulk of the Niacin is releasing within 2 to 3 hours from this tablet. Following is the formula exhibiting the release pattern indicated by the sustained released assay below:

| Each tablet contains: | Wt. | % |
|---|---|---|
| Guar Gum (granulated)* | 450 mg. | 37.19 |
| Niacin (granulated)* | 212 mg. | 17.769 |
| Calcium Carbonate | 200 mg. | 14.463 |
| Microcrystalline Cellulose (M.C.C.) | 150 mg. | 12.397 |
| Citric Acid | 60 mg. | 4.958 |
| Dextrose | 50 mg. | 4.545 |
| Oat Fiber | 50 mg. | 4.132 |
| Magnesium Oxide | 25 mg. | 2.066 |
| Silicon Dioxide | 15 mg. | 1.240 |
| Magnesium Stearate | 15 mg. | 1.240 |

*The Niacin particles are coated in a fluid bed granulator and are 95% Niacin comprising a first coating or film of 3% NACMC (Sodium Carboxymethylcellulose) followed by a subsequent coating or film of 2% Surelease, a polymeric dispersion of ethylcellulose (Colorcon 7060). A guar gum granulate is made comprising Aqualon Supercol G3 Guar Gum and sprayed with NACMC (Sodium Carboxymethylcellulose, 1.8%, at 7.5% solids in solution). The NACMC coating or film in both applications is Aqualon 7L2P).

Sustained Release Assay

| Time (Hours) | Percent Released | Mg./Tab |
|---|---|---|
| 1 | 38 | 76.2 |
| 2 | 47 | 94.3 |
| 3.5 | 9 | 17.9 |
| 5 | 4 | 9.2 |
| 7 | 3 | 6.9 |
| 8 | 1 | 2.1 |

Other fibers, drugs, mineral salts, acids, and soluble sugars may replace those employed in the foregoing Example, although the acid and the soluble sugar may be dispensed with and prolonged-release operativeness still retained, as fully explained elsewhere herein. The acid is optional but is advantageously provided when a quicker release of the therapeutic agent is desired. Moreover, a composition of the foregoing Example, wherein only the gel-forming fiber is precoated and not the therapeutic agent, is found to be superior to the same composition wherein neither the gel-forming fiber nor the therapeutic agent are precoated, but the same composition wherein both the gel-forming fiber and the therapeutic agent are precoated is highly advantageous especially when a quick-controlled release tablet, such as illustrated by Example 1, is desired.

If a longer controlled release is desired, standard wet granulation of the ingredients yields an 8-hour release curve. It is apparent that it is not necessary to precoat the gel-forming fiber or gum to obtain a longer release profile. Again the drug in the following example is Niacin:

EXAMPLE 2

Longer Controlled-Release Tablet

Each tablet contains:

| Guar Gum* | 500 mg. |
|---|---|
| Niacin* | 200 mg. |
| Calcium Carbonate | 200 mg. |
| Microcrystalline Cellulose | 150 mg. |
| Dextrose | 50 mg. |
| Magnesium Oxide | 25 mg. |
| Silicon Dioxide | 15 mg. |
| Magnesium Stearate | 15 mg. |

*not precoated

Sustained-Release Assay of Example 2

| Time | % Release |
|---|---|
| 1 Hour | 8.68 |
| 2 Hours | 9.88 |
| 3.5 Hours | 11.24 |
| 5 Hours | 15.85 |
| 7 Hours | 27.74 |
| 8 Hours | 32.10 |

As can be seen, the release time for the bulk of the product of this Example is delayed considerably as compared with the product of Example 1, e.g., into the second half of an eight-hour period.

Other fibers, drugs, mineral salts, and soluble sugars may obviously replace those employed in the foregoing Example, although the soluble sugar may be dispensed with and prolonged-release operativeness still retained, as fully explained elsewhere herein.

Moreover, the composition of the foregoing Example, wherein the gel-forming fiber is precoated with hydrocolloid, as in Example 1, is found to be superior to the same composition wherein neither the gel-forming fiber nor the therapeutic agent are precoated, but the same composition wherein both the gel-forming fiber and the therapeutic agent are precoated is highly advantageous especially when a quick-controlled release tablet, such as illustrated by Example 1, is desired.

In both Examples, photographs show that the tablet appearance after 8 hours is a slightly enlarged, gelled version of its original shape, indicating that the drug has been released out of a matrix of the coated gel-forming guar gum without complete disintegration or dispersion of the fiber being necessary. The products of both Example 1 and Example 2 comprise a fiber-matrix which retains its integrity and passes through the intestinal tract and is eliminated through the bowels. Such expendable gel-fiber controlled-release tablet can be designed to release the active drug contained therein either quickly or slowly. This provides the ability to release a drug in the small intestine, which should be about 5 hours after ingestion. The gel-fiber matrix also exhibits viscosity which slows its passage through the gastrointestinal tract, allowing for smoother release of a drug as well as for the gel to act as an excellent antacid-like protective agent, buffering the contact of the drug with the intestinal lining. It is precisely this property which allows for improved delivery of certain analgesics such as Aspirin and Ibuprofen and other nonsteroidal anti-inflammatory drugs (NSAIDs) as given in the examples which follow:

EXAMPLE 3

NSAID Controlled-Release Tablet

Each tablet contains:

| Coated Guar Gum* | 450 mg. |
|---|---|
| Coated Ibuprofen* | 212 mg. |
| Calcium Carbonate | 200 mg. |
| Microcrystalline Cellulose | 150 mg. |

-continued

| | |
|---|---|
| Dextrose | 50 mg. |
| Silicon Dioxide | 15 mg. |
| Magnesium Stearate | 15 mg. |

*The Ibuprofen is coated in a fluid bed granulator and is 95% Ibuprofen comprising a first coating of 3% NACMC (Sodium Carboxymethylcellulose) followed by a subsequent coating of 2% Surelease, a polymeric dispersion of ethylcellulose (Colorcon 7060). A guar gum granulate is made comprising Aqualon Supercol G3 Guar Gum sprayed with NACMC (Sodium Carboxymethylcellulose, 1.8%, at 7.5% solids in solution). The NACMC coating in both applications is Aqualon 7L2P.

Upon administration, the release time is similar to that shown in Example 1. Irritation of the gastrointestinal tract is substantially reduced.

Other fibers, drugs, mineral salts, and soluble sugars may obviously replace those employed in the foregoing Example, although the soluble sugar may be dispensed with and prolonged-release operativeness, but with somewhat greater delay in release, still retained, as fully explained elsewhere herein.

Moreover, the composition of the foregoing Example, wherein only the gel-forming fiber is precoated and not the therapeutic agent, is found to be superior to the same composition wherein neither the gel-forming fiber nor the therapeutic agent are precoated, but the same composition wherein both the gel-forming fiber and the therapeutic agent are precoated is highly advantageous especially when a quick-controlled release tablet, such as illustrated by Example 1, is desired.

The same formula can be advantageously repeated substituting Aspirin or other nonsteroidal anti-inflammatory drugs which irritate the gastrointestinal tract and with equally favorable results.

The above formulation can be manufactured without the use of or with a smaller amount of the coated guar gum, but wider degrees of control and improved hydration can be achieved using a higher amount of fiber and a precoated fiber as indicated.

EXAMPLE 4

Minimum Ratio Example (600:1) (Small Amount of Drug)

Each tablet contains:

| | |
|---|---|
| Coated Guar Gum (as per Example 1) | 300 mg. |
| Vitamin B-12 | 500 mcg. |
| Calcium Carbonate | 100 mg. |
| Dextrose | 100 mg. |
| Microcrystalline Cellulose | 100 mg. |
| Magnesium Stearate | 15 mg. |
| Silicon Dioxide | 15 mg. |

Other fibers, drugs, mineral salts, and soluble sugars may obviously replace those employed in the foregoing Example, although the soluble sugar may be dispensed with and prolonged-release operativeness still retained, as fully explained elsewhere herein.

EXAMPLE 5

Maximum Ratio Example (1:2) (large Amount of Drug)
Each tablet contains:

| | |
|---|---|
| Coated Guar Gum (as per Example 1) | 300 mg. |
| Gemfibrozil | 600 mg. |
| Calcium Carbonate | 50 mg. |
| Dextrose | 25 mg. |
| Magnesium Stearate | 15 mg. |

Other fibers, drugs, mineral salts, and soluble sugars may obviously replace those employed in the foregoing Example, although the soluble sugar may be dispensed with completely and prolonged-release operativeness, although somewhat slower, still retained, as fully explained elsewhere herein.

Moreover, the composition of the foregoing Example, wherein only the gel-forming fiber is precoated and not the therapeutic agent, is found to be superior to the same composition wherein neither the gel-forming fiber nor the therapeutic agent are precoated, but the same composition wherein both the gel-forming fiber and the therapeutic agent are precoated is highly advantageous especially when a quick-controlled release tablet, such as illustrated by Example 1, is desired.

Drug Carrier System for Proteins and Peptides (Protection of Drugs From Proteolytic Enzymes)

An additional characteristic of the invention is its ability to at least partially protect a drug or therapeutic peptide or protein from degradation by proteolytic enzymes. Proteolytic enzymes formed in the gastrointestinal tract hydrolyze peptides, proteins, amides, and esters, etc., degrading them and destroying their activity as macromolecules. Drugs such as Insulin must therefore be injected directly into the bloodstream. The oral delivery of peptides could dramatically impact health care over the next ten years, and would be a preferable mode of administering these drugs compared to injection. Therapeutic peptides that are presently injected are drugs such as heparin, insulin, calcitonin, erythropoietin, granulocytecolony stimulating factors, growth hormones, S.O.D., and interferon. By employing the gel-fiber matrix controlled-release system herein, these macromolecules can be protected from destruction by proteolytic enzymes.

Dietary fibers such as guar gum and pectin have been shown to inhibit pancreatic enzyme activities (Isaksson G., et al., Digestion 24: 54–59, 1982). Trypsin, lipase, phospholipase, and amylase activities were inhibited by these and other dietary fibers. By employing the gel-fiber matrix controlled-release system herein, containing a pancreatic enzyme-inhibitory amount of the gel-forming dietary fiber, e.g., guar gum, these macromolecules can be protected from destruction by proteolytic enzymes so that they can be delivered as microspheres at the appropriate point in the gastrointestinal tract where they can be properly absorbed. Encapsulation of these drugs within a biodegradable polymeric capsule or microsphere can protect them from further proteolytic degradation so that they can remain biologically active after passage through the intestinal mucosa.

One example is polyalkylcyanoacrylate nanocapsules with an average size of 220 NM which have been successfully used as a drug carrier for orally-administered insulin. By embedding these nanocapsules in the gel-fiber matrix of this invention, one is able to offer improved protection from damaging enzymes as well as delivery of these nanoparticles to the small intestine.

EXAMPLE 6

Drug Carrier System for Peptides in Nanospheres
Each tablet contains:

| | |
|---|---|
| Coated Guar Gum (as per Example 1) | 200 mg. |
| *Polyalkylcyanoacrylate Nanocapsules of Superoxide Dismutase (SOD) | 100 mcg. |
| Calcium Carbonate | 100 mg. |
| Microcrystalline Cellulose | 50 mg. |

| Magnesium Stearate | 15 mg. |

*Polyalkylcyanoacrylate nanocapsules are spherical vesicles less than 300 NM in diameter that are prepared according to the method of Al Khouri et al., Int. J. Pharm. 28:125-132, 1986.

Other fibers, drugs, and mineral salts, and other polymers, e.g., cellulose polymers for the nanocapsules or microspheres employed, may obviously replace those employed in the foregoing Example.

Drug Carrier for Liposoluble Drugs and Vitamins

A further benefit of the gel-fiber matrix is its ability to entrap or embed lipid-soluble drugs and vitamins or to serve as an entrapment matrix for liposomes. By spray drying the gel-forming fiber with a fat-soluble drug, the lipid is entrapped in the fiber and can subsequently be formed into a solid dosage form which has the lipid-soluble drug embedded in the gel-fiber matrix. Alternatively, the liposoluble drug may be pressed into the gel-forming fiber powder prior to formation of the solid dosage form. It is generally known that lipids are solubilized by biliary salts in the intestinal lumen after pancreatic lipase has acted on the emulsion. These micelles are then absorbed at the microvilli through transmembrane diffusion.

EXAMPLE 7

Liposoluble Drug Delivery

A spray dried powder is formed using guar gum as the carrier and beta-Carotene as the fat-soluble drug or vitamin. This powder containing the beta-Carotene embedded in the guar gum is then made into the following tablet:

Each tablet contains:

| Guar Gum | 450 mg. |
| Beta-Carotene | 25,000 I.U. |
| Calcium Carbonate | 200 mg. |
| Microcrystalline Cellulose | 150 mg. |
| Dextrose | 50 mg. |
| Magnesium Stearate | 15 mg. |

The beta-carotene/guar gum mixture can also be made by pressing or grinding beta-carotene in a soybean oil base into the guar gum powder using a mortar and pestle or a roller press system. This results in a free-flowing powder consisting of a fat-soluble vitamin or drug embedded in a coated gel-forming fiber which can then be formed into a solid dosage form. Normally, liposoluble vitamins or drugs must be encapsulated in soft gelatin capsules, and are not manufactured as tablets, granules, or other solid dosage forms. Furthermore, once these soft gelatin capsules dissolve in the stomach, they release essentially all of the active drug or vitamin. The present invention allows for the controlled-release of these liposoluble therapeutic agents. Other gums or gel-forming fibers may also be used in the same way.

Other mineral salts and soluble sugars may obviously replace those employed in the foregoing Example, although the soluble sugar may be dispensed with and prolonged-release operativeness still retained, as fully explained elsewhere herein.

EXAMPLE 8

Tablets are made according to the following formula:

| Guar Gum | 400 mg | |
| Aspirin | 200 mg | |
| Calcium Carbonate | 100 mg | optional |
| Dextrose | 50 mg | optional |
| Citric Acid | 25 mg | optional |
| Microcrystalline-Cellulose (MCC) | 25 mg | |

The guar gum fiber forms a sphere or plug of hydrated gel which coats the aspirin and from which the aspirin slowly leaches as the gel hydrates and passes through the gastrointestinal tract, aided by the citric acid and calcium carbonate as disintegrants. The gel-forming fiber also assists in minimizing the caustic effect of the aspirin when it comes into full contact with the stomach, because the "gel plug" or sphere of fiber-gel insulates the aspirin as well as modulates its release.

Other fibers, drugs, mineral salts, acids, and soluble sugars may obviously replace those employed in the foregoing Example, although the acid and the soluble sugar may be dispensed with and prolonged-release operativeness still retained, as fully explained elsewhere herein. Moreover, a composition of the foregoing Example, wherein only the gel-forming fiber is precoated and not the therapeutic agent, is found to be superior to the same composition wherein neither the gel-forming fiber nor the therapeutic agent are precoated, but the same composition wherein both the gel-forming fiber and the therapeutic agent are precoated is highly advantageous especially when a quick-controlled release tablet, such as illustrated by Example 1, is desired.

EXAMPLE 9

Tablets are made by compression at usual pressures of 4,000 to 10,000 pounds per square inch according to the following formula:

Each Table Contains:

| Locust Bean Gum* | 150 mg |
| Acacia Gum* | 50 mg |
| Karaya Gum* | 100 mg |
| Tragacanth Gum* | 50 mg |
| Carrageenan* | 50 mg |
| Vitamin C | 250 mg |
| Calcium Carbonate | 100 mg |
| Dextrose** | 25 mg |
| Citric Acid** | 25 mg |
| Microcrystalline-Cellulose | 25 mg |
| Polyvinylpyrrolidone (crosslinked)-(Povidone TM) | 15 mg |

*Preferably coated as per Example 1; or one or more gum is preferably used to coat the others, in a fluid-bed granulator, or according to the procedure of Examples 1 or 19-21.
**Optional Other fibers, drugs, mineral salts, acids, and soluble sugars may obviously replace those employed in the foregoing Example, although the acid and the soluble sugar may be dispensed with and prolonged-release operativeness still retained, as fully explained elsewhere herein. Moreover, a composition of the foregoing Example, wherein only the gel-forming fiber is precoated and not the therapeutic agent, is found to be superior to the same composition wherein neither the gel-forming fiber nor the therapeutic agent are precoated, but the same composition wherein both the gel-forming fiber and the therapeutic agent are precoated is highly advantageous especially when a quick-controlled release tablet, such as illustrated by Example 1, is desired.

EXAMPLE 10

| Stimulant tablet | |
| --- | --- |
| Guar Gum* | 500 mg |
| Caffeine | 100 mg |
| Calcium Carbonate | 200 mg |
| Citric Acid** | 75 mg |
| Lactose (Anhydrous)** | 50 mg |
| Microcrystalline-Cellulose (MCC) | 25 mg |

*Preferably coated as per Example 1
**Optional

Other fibers, drugs, mineral salts, acids, and soluble sugars may obviously replace those employed in the foregoing Example, although the acid and the soluble sugar may be dispensed with and prolonged-release operativeness still retained, as fully explained elsewhere herein.

Moreover, the composition of the foregoing Example, wherein only the gel-forming fiber is precoated and not the therapeutic agent, is found to be superior to the same composition wherein neither the gel-forming fiber nor the therapeutic agent are precoated, but the same composition wherein both the gel-forming fiber and the therapeutic agent are precoated is highly advantageous especially when a quick-controlled release tablet, such as illustrated by Example 1, is desired.

EXAMPLE 11

| Weight-Loss tablet (Appetite Suppressant) | |
| --- | --- |
| Guar Gum* | 500 mg |
| Phenylpropanolamine base | 5 mg |
| Calcium Carbonate | 200 mg |
| Citric Acid** | 75 mg |
| Dextrose** | 50 mg |
| Microcrystalline-Cellulose (MCC) | 30 mg |

*Preferably coated as per Example 1
**Optional

The coated guar gum expands 3 to 4 times its original size in the stomach, and gives the subject a full feeling, while the phenylpropanolamine tends to shut off the hunger signal in the brain. These two principal ingredients work together to produce a dual action on the two primary components of a weight loss product, satiety and hunger, while the guar gum also serves to modulate the absorption of the phenylpropanolamine, prolonging its action.

Other fibers, drugs, mineral salts, acids, and soluble sugars may obviously replace those employed in the foregoing Example, although the acid and the soluble sugar may be dispensed with and prolonged-release operativeness still retained, as fully explained elsewhere herein.

EXAMPLE 12

Tablets are made according to the following formula:

| Each Tablet Contains | |
| --- | --- |
| Psyllium seed husks - powdered* | 500 mg |
| Niacin | 100 mg |
| Calcium carbonate | 150 mg |
| Dextrose** | 50 mg |
| Citric acid** | 25 mg |
| Microcrystalline cellulose (Avicel ™) | 25 mg |

*Preferably coated as per Example 1
**Optional

The calcium carbonate and, when present, the citric acid, act to mechanically disperse the coated gel-forming psyllium fiber which acts as a drug delivery system for the niacin. The psyllium fiber also serves to coat the niacin, minimizing its acidic effect on the stomach lining and intestines.

In the foregoing formulation, some or all of the psyllium seed husk powder may be replaced by another gel-forming dietary fiber, e.g., guar gum or one or more of the gums used in Example 13, pectin or a pectic substance, algal polysaccharides, glucomannan, agar, lignin, or the like, or combinations thereof, with essentially the same result.

Other fibers, drugs, mineral salts, acids, and soluble sugars may obviously replace those employed in the foregoing Example, although the acid and the soluble sugar may be dispensed with and prolonged-release operativeness still retained, as fully explained elsewhere herein.

Moreover, the composition of the foregoing Example, wherein only the gel-forming fiber is precoated and not the therapeutic agent, is found to be superior to the same composition wherein neither the gel-forming fiber nor the therapeutic agent are precoated, but the same composition wherein both the gel-forming fiber and the therapeutic agent are precoated is highly advantageous especially when a quick-controlled release tablet, such as illustrated by Example 1, is desired.

EXAMPLE 13

Tablets are made according to the following formula:

| Each Tablet Contains | |
| --- | --- |
| Locust bean gum* | 100 mg |
| Acacia gum* | 100 mg |
| Gum arabic* | 100 mg |
| Xanthan gum* | 100 mg |
| Karaya gum* | 50 mg |
| Tragacanth gum* | 50 mg |
| Niacin | 100 mg |
| Calcium carbonate | 150 mg |
| Dextrose** | 50 mg |
| Citric Acid** | 25 mg |
| Microcrystalline cellulose (Avicel ™) | 25 mg |

*Preferably coated as per Example 1; or one or more gum is preferably used to coat the others in a fluid-bed granulator, or in accord with the procedure of Examples 1 or 19-21.
**Optional In the foregoing formulation, one or more of the coated gums may be replaced by another gel-forming dietary fiber, e.g., psyllium seed husks, pectin or a pectic substance, algal polysaccharides, glucomannan, agar, lignin, or the like, or combinations thereof, with essentially the same result. These tablets, as well as those of the foregoing Example 13, are found to be effective in lowering cholesterol levels at effective doses of niacin without the usual side effects of flushing, itching, and irritation.

Other fibers, drugs, mineral salts, acids, and soluble sugars may obviously replace those employed in the foregoing Example, although the acid and the soluble sugar may be dispensed with and prolonged-release operativeness still retained, as fully explained elsewhere herein.

Moreover, the composition of the foregoing Example, wherein only the gel-forming fiber is precoated and not the therapeutic agent, is found to be superior to the same composition wherein neither the gel-forming fiber nor the therapeutic agent are precoated, but the same composition wherein both the gel-forming fiber and the therapeutic agent are precoated is highly advantageous especially when a quick-controlled release tablet, such as illustrated by Example 1, is desired.

EXAMPLE 14

A niacin granulate is produced in a fluid-bed granulator (Glatt Air Techniques, Ramsey, N.J.). The niacin is first sprayed with NaCMC (Sodium Carboxymethylcellulose) at 7.5% solids in solution level, and 3% by weight volume percentage. While still in the fluid bed granulator, the coated niacin is then sprayed with Surelease (TM) (Colorcon, West Point, PA.), an ethyl cellulose preparation, at 15% solids in solution and 2% by weight volume percentage. The gel-forming fiber is coated in the same manner.
Prepare 95% Niacin Granulation
In granulator bowl—Niacin powder.
In solution—Spray first with NaCMC, 7.5% solids in solution, 3% by weight volume percentage. Spray second with Surelease (TM) (ethyl cellulose) 15% solids, 2% by weight volume percentage.

The 95% niacin granulate is then used in the following formula:

| Each Tablet Contains | |
| --- | --- |
| Psyllium husk powder (coated) | 600 mg |
| Niacin granulate (95%) | 160 mg |
| Calcium carbonate | 100 mg |
| Citric Acid (optional) | 25 mg |
| Microcrystalline cellulose (Avicel TM) | 25 mg |

In the foregoing formulation, some or all of the psyllium seed husk powder may be replaced by another gel-forming dietary fiber, e.g., guar gum or one or more of the gums used in Example 13, pectin or a pectic substance, algal polysaccharides, glucomannan, agar, lignin, or the like, or combinations thereof, with essentially the same result.

Other cellulose coatings or other hydrocolloid coatings, including hydrocolloids such as, e.g., natural and modified gums, celluloses and modified celluloses, pectin, mucillages, modified starches, noncellulosic polysaccharides, algal polysaccharides and mixtures thereof, may replace those used in the foregoing.

A much higher dose of niacin is found to be possible by granulating the niacin before tableting so that it is released more slowly. A subject can take two tablets of the above formula with virtually no side effects such as the severe flushing, itching, or gastric distress produced by normal niacin.

The tablet ingredients may also be formed into granules, if desired, and then may be taken alone, without tableting, if desired, in effective dosages, but this is generally less convenient from the standpoint of the user and less advantageous from the standpoint of prolonged time-release effect upon ingestion.

Dextrose or other soluble sugar may also be present in an amount up to about 100 mg if desired, to further assist in tablet disintegration upon ingestion.

EXAMPLE 15

A capsule example is:

| | |
| --- | --- |
| Guar Gum (coated) | 500 mg |
| Magnesium Carbonate | 80 mg |
| Niacin | 80 mg |
| Citric Acid (fine powder) (optional) | 10 mg |

Other fibers, drugs, mineral salts, and acids may obviously replace those employed in the foregoing Example.

EXAMPLE 16

| Minimum Ratio Example (600:1) (small amount of drug) | |
| --- | --- |
| Guar Gum (coated) | 300 mg |
| Vitamin B-12 | 500 mcg |
| Calcium Carbonate | 100 mg |
| Citric Acid (optional) | 50 mg |
| Dextrose (optional) | 100 mg |
| MCC | 25 mg |

Other fibers, drugs, mineral salts, acids, and soluble sugars may obviously replace those employed in the foregoing Example.

EXAMPLE 17

| Maximum Ratio Example (1:2) (large amount of drug) | |
| --- | --- |
| Each tablet contains: | |
| Guar Gum (coated) | 350 mg |
| Ibuprofen | 700 mg |
| Calcium Carbonate | 50 mg |
| Citric Acid (optional) | 50 mg |
| Dextrose (optional) | 50 mg |
| MCC | 25 mg |

Other fibers, drugs, mineral salts, acids, and soluble sugars may obviously replace those employed in the foregoing Example.

EXAMPLE 18

Pharmacological Evaluation Dissolution Test The tablets from Example 9 are dissolved in a gastric simulator dissolution apparatus at 0.1N HCl and are observed to take on the appearance of "cotton plugs" or balls of fiber-gel from which the Vitamin C is slowly released. Samples are taken from each vessel at 1, 4, and 6 hours and the Vitamin C content from each is analyzed. The results confirm that the Vitamin C is being slowly released over time from the fiber-gel matrix. Similar tests on other products of the invention likewise confirm the steady prolonged and efficient release of the drug or other therapeutic agent over a prolonged period but with ultimate release of substantially all of the active ingredient within the gastrointestinal tract.

EXAMPLE 19

Niacin Tablet-Coating Variations

Each tablet contains:

| | |
|---|---|
| Guar Gum* | 450 mg. |
| Niacin* | 212 mg. |
| Calcium Carbonate | 200 mg. |
| Microcrystalline Cellulose (MCC) | 150 mg. |
| Lactose | 50 mg. |
| Silicon Dioxide | 15 mg. |
| Magnesium Stearate | 15 mg. |

*Coated with gum arabic or gelatin

The guar gum is coated in a fluid-bed granulator with gum arabic (acacia gum) at 1.5%. The niacin is coated with sodium carboxymethylcellulose and ethylcellulose at 3% and 2% levels respectively.

The same formula can be duplicated but with the coating on the guar gum being gelatin at a 5% level (225 bloom gelatin).

EXAMPLE 20

Chromium Deficiency Tablet Formulation
Each tablet contains:

| | |
|---|---|
| Guar Gum (coated)* | 200 mg. |
| Sodium Carboxymethylcellulose (crosslinked) | 50 mg. |
| Calcium Carbonate | 50 mg. |
| Lactose | 50 mg. |
| DiCalcium Phosphate | 50 mg. |
| Silicon Dioxide | 10 mg. |
| Magnesium Stearate | 5 mg. |
| Chromium Chloride or Chromium Polynicotinate | 100 mcg. |

*The guar gum is precoated with an ethyl-cellulose coating at 1.5% in a fluid-bed granulator and is therefore 98.5% guar gum.

The product is useful to reduce serum cholesterol in individuals who are deficient in chromium as well as to provide a source of chromium for diabetics.

EXAMPLE 21

Cardiovascular Tablet Formulation
Each tablet contains:

| | |
|---|---|
| Guar Gum* | 450 mg. |
| Sodium Carboxymethylcellulose (cross-linked) | 100 mg. |
| Calcium Carbonate | 50 mg. |
| DiCalcium Phosphate | 150 mg. |
| Magnesium Oxide | 250 mg. |
| Silicon Dioxide | 15 mg. |
| Magnesium Stearate | 15 mg. |

*Coated with 1.7% sodium carboxymethylcellulose in a fluid-bed granulator.

The product is useful for therapeutic cardiovascular purposes, e.g., for vasospasm reduction, as an antithrombotic, or in cholesterol reduction.

Drugs or Therapeutic Agents

Among drugs or therapeutic agents which may be incorporated according to this invention, but to which it should not be limited, are:
  a. Antipyretics, and nonsteroidal anti-inflammatory drugs (NSAIDs), and analgesics such as acetaminophen, aspirin and ibuprofen
  b. Appetite suppressants such as phenylpropanolamine hydrochloride and stimulants such as caffeine
  c. Potassium, KCl , or another mineral supplement
  d. Water-soluble vitamins and fat-soluble vitamins, e.g., Vitamin C
  e. Vitamin B-12
  f. Antihypercholesterolemics, and especially Gemfibrozil and Niacin
  g. Antitussives, such as dextromethorphan, dextromethorphan hydrobromide, noscapine, carbetapentane citrate, and chlophedianol hydrochloride.
  h. Antihistamines, such as chlorpheniramine maleate, phenindamine tartrate, pyrilamine maleate, doxylamine succinate, and phenyltoloxamine citrate.
  i. Decongestants, such as phenylephrine hydrochloride, phenylpropanolamine hydrochloride, pseudoephedrine hydrochloride, and ephedrine.
  j. Therapeutic peptides such as Heparin derivatives, insulin, calcitonin, erythropoietin, superoxide dismutase, granulocyte colony-stimulating factors, growth hormones, and interferon.

Preferred particular drugs, minerals, or vitamins for which the present delivery system is ideally suited include:

Niacin, Vitamin B-12, Potassium Chloride, Vitamin C, Aspirin, Caffeine, Phenylpropanolamine hydrochloride, Ibuprofen, Pseudoephedrine, Nitroglycerin, and Gemfibrozil.

The active ingredient can be any type of medication which acts systemically and which can be administered orally to transmit the active therapeutic agent into the gastrointestinal tract and into the bloodstream in therapeutically-effective levels without early excessive peak concentrations, without being inactivated by physiological fluids, and without passing unchanged through the body of the patient or subject by being excreted unabsorbed. Alternatively, the active ingredient can be any type of medication which acts through the buccal tissues of the mouth to transmit the active ingredient directly into the bloodstream, thus bypassing both any possible first pass liver metabolism and/or the gastric and intestinal fluids, which often have an adverse inactivating or destructive action on the active ingredient unless it is specially protected against such fluids as by means of an enteric coating or the like. The active ingredient can also be a type of medication which can be transmitted into the blood circulation through the rectal tissues.

Representative active therapeutic agents include antacids, anti-inflammatory substances, coronary dilators, cerebral dilators, vasodilators, antibacterials, psychotropics, antimanics, stimulants, antihistamines, laxatives, decongestants, vitamins, and the like. However, it is to be understood that the invention is also applicable to sublingual lozenges, suppositories, capsules and compressed tablets, the latter being intended to be swallowed in unit dosage form and which, upon ingestion according to a prescribed regimen, give slow and regular release of active therapeutic agent without an initial dumping of a fixed percentage in the intestinal tract while being protected against normally-inactivating gastric fluids, whether administered for therapeutic, preventive, or dietary purposes, and whether employed in human or veterinary therapy.

It is therefore seen that the present invention provides a unique prolonged-release dosage formulation, especially a tablet, consisting of the following as essential ingredients: an effective dose of a biologically-absorbable drug or other therapeutic agent, preferably coated with a hydrocolloid, a gel-forming fiber, such as guar gum, preferably coated with a hydrocolloid, a mineral salt which releases a physiologically-acceptable gas upon ingestion, preferably a mineral carbonate or bicarbonate, optionally a physiologically-acceptable acid, especially a food-grade organic acid or phosphoric acid, and optionally and advantageously dextrose or another soluble sugar as a further disintegrant, and a method of controllably prolonging the release of a drug or other active therapeutic agent upon administration to a living animal body, e.g., a human being or other animal, by employment of such a prolonged-release pharmaceutical, therapeutic, or dietary composition, all having the unpredictable and highly advantageous characteristics and effects as more fully set forth in the foregoing.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can be legally accorded to the appended claims.

I claim:

1. A solid prolonged release oral unit dosage composition for oral administration and ingestion in solid form, and intended to be swallowed as such, which consists essentially of a solid admixture of an effective dose of particles of a biologically-absorbable therapeutic agent or drug, gel-forming dietary matrix particles, a mineral salt of carbonate or bicarbonate which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, wherein the gel-forming dietary fiber comprises about 35% to about 50% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being coated with a hydrocolloid film and the therapeutic agent or drug particles being optionally coated with a film of the same or a different hydrocolloid.

2. A method for prolonging the release of a drug or therapeutic agent upon oral ingestion by a human being, comprising the step of orally administering to the said human being a prolonged release unit dosage oral composition which consists essentially of a solid admixture of an effective dose of particles of a biologically-absorbable therapeutic agent or drug, gel-forming dietary matrix particles, a mineral salt of carbonate or bicarbonate which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, wherein the gel-forming dietary fiber comprises about 35% to about 50% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being coated with a hydrocolloid film and the therapeutic agent or drug particles being optionally coated with a film of the same or a different hydrocolloid.

3. A solid prolonged release oral unit dosage composition for oral administration and ingestion in solid form, and intended to be swallowed as such, which consists essentially of a solid admixture of an effective dose of particles of a biologically-absorbable therapeutic agent or drug, gel-forming dietary matrix particles, a mineral salt of carbonate or bicarbonate which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, wherein the gel-forming dietary fiber comprises about 35% to about 50% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being optionally coated with a hydrocolloid film and the therapeutic agent or drug particles being optionally coated with a film of the same or a different hydrocolloid.

4. A solid prolonged-release oral unit dosage composition for oral administration and ingestion in solid form, and intended to be swallowed as such, which consists essentially of a solid admixture of an effective dose of particles of a biologically-absorbable therapeutic agent or drug, gel-forming dietary fiber matrix, a mineral salt carbonate or bicarbonate which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, wherein the gel-forming dietary fiber comprises about 30 to about 40% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being coated with a hydrocolloid film and the therapeutic agent or drug particles being optionally coated with a film of the same or a different hydrocolloid.

5. A solid prolonged-release oral unit dosage composition for oral administration and ingestion in solid form, and intended to be swallowed as such, which consists essentially of a solid admixture of an effective dose of particles of a biologically-absorbable therapeutic agent or drug, gel-forming dietary fiber matrix, a mineral salt carbonate or bicarbonate which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, wherein the gel-forming dietary fiber comprises about 10% to about 85% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being coated with a cellulose polymer coating and the therapeutic agent or drug particles being optionally coated with a film of the same or a different cellulose polymer coating.

6. The composition of claim 5, wherein the drug or therapeutic agent is in granular form, the granules being coated with a film of a cellulose polymer, the composition optionally being compressed into a tablet form.

7. A method for prolonging the release of a drug or therapeutic agent upon oral ingestion by a human being, comprising the step of orally administering to the said human being a prolonged-release unit dosage oral composition in solid form which consists essentially of a solid admixture of an effective dose of particles of a biologically-absorbable therapeutic agent or drug, a gel-forming dietary fiber matrix particle, a mineral salt carbonate or bicarbonate which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, where the gel-forming dietary fiber comprises about 30% to about 40% by weight, the mineral salt comprises about 5% to about 75% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being coated with a hydrocolloid film and the therapeutic agent or drug particles being optionally coated with a film of the same or a different hydrocolloid.

8. A method for prolonging the release of a drug or therapeutic agent upon oral ingestion by a human being, comprising the step of orally administering to the said human being a prolonged-release unit dosage oral composition in solid form which consists essentially of a solid admixture of an effective dose of particles of a biologically-absorbable therapeutic agent or drug, a gel-forming dietary fiber matrix particle, a mineral salt carbonate or bicarbonate which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, where the gel-forming dietary fiber comprises about 10% to about 85% by weight, the mineral salt comprises about 5% to about 75% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being coated with a cellulose polymer coating and the therapeutic agent or drug particles being optionally coated with a film of the same or a different cellulose polymer coating.

9. The method of claim 8, wherein the drug or therapeutic agent is in granular form, the granules being coated with a film of a cellulose polymer, the composition optionally being compressed into a tablet form.

10. A solid prolonged-release oral unit dosage composition for oral administration and ingestion in solid form, and intended to be swallowed as such, such consists essentially of a solid admixture of an effective dose of a biologically absorbable therapeutic agent or drug, a gel-forming dietary fiber matrix, a mineral salt which releases a physiologically-acceptable gas upon ingestion, and a physiologically-acceptable acid, the combination of the fiber and mineral salt providing amounts thereof which effect prolonged but effective release of the drug or therapeutic agent upon oral ingestion and exposure of the solid composition to biological fluids, wherein the gel-forming dietary fiber comprises about 30% to about 40% by weight, the mineral salt comprises about 5% to about 75% by weight, the physiologically-acceptable acid comprises 0% to about 50% by weight, and the ratio of the weight of the gel-forming fiber to the weight of the drug or therapeutic agent is between about 1,000:0.5 and 1:1.5, the gel-forming dietary fiber particles being optionally coated with a hydrocolloid film and the therapeutic agent or drug particles being optionally coated with a film of the same or a different hydrocolloid.

* * * * *